United States Patent

Jonas et al.

[11] Patent Number: 5,276,027
[45] Date of Patent: Jan. 4, 1994

[54] THIADIAZINONES

[75] Inventors: Rochus Jonas, Darmstadt; Michael Klockow, Rossdorf; Joachim Leibrock, Pfungstadt; Hans-Jochen Schliep, Mühltal-Traisa; Christoph Seyfried, Seeheim-Jugenheim; Michael Wolf, Darmstadt, all of Fed. Rep. of Germany

[73] Assignee: Merck Patent Gesellschaft Mit Beschrankter Haftung, Darmstadt, Fed. Rep. of Germany

[21] Appl. No.: 964,686

[22] Filed: Oct. 22, 1992

[30] Foreign Application Priority Data

Oct. 23, 1991 [DE] Fed. Rep. of Germany ....... 4134893

[51] Int. Cl.$^5$ .................... A61K 31/54; C07D 285/16
[52] U.S. Cl. ...................... 514/222.5; 544/8
[58] Field of Search .................. 544/8; 514/222.5

[56] References Cited

U.S. PATENT DOCUMENTS 4,916,128 4/1990 Jonas et al. .................. 514/213

FOREIGN PATENT DOCUMENTS 80296 11/1982 European Pat. Off. .

Primary Examiner—John M. Ford
Attorney, Agent, or Firm—Millen, White, Zelano & Branigan

[57] ABSTRACT

Compounds of formula I

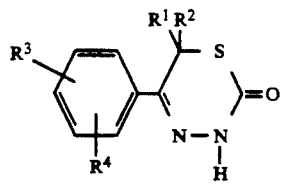

in which
$R^1$ and $R^2$ are each independently of one another H or A,
$R^3$ is H, OA or $O-C_mH_{2m+1-n}X_n$,
$R^4$ is $-O-C_mH_{2m+1-n}X_n$,
X is F or Cl,
A is alkyl having 1-6 C atoms,
m is 1, 2, 3, 4, 5 or 6 and
n is 1, 2, 3, 4, 5, 6, 7, 8, 9, 10, 11, 12 or 13, and their salts have positive ionitropic activity and vasodilating action, and promote circulation. In addition, the compounds can be employed for the treatment of asthmatic disease and memory disorders, and have antidepressive and anti-inflammatory properties.

11 Claims, No Drawings

THIADIAZINONES

SUMMARY OF THE INVENTION

The invention relates to novel thiadiazinone derivatives of the formula I

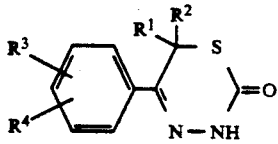

in which
$R^1$ and $R^2$ are each independently of one another H or A,
$R^3$ is H, OA or $O-C_mH_{2m+1-n}X_n$,
$R^4$ is $-O-C_mH_{2m+1-n}X_n$,
X is F or Cl,
A is alkyl having 1–6 C atoms,
m is 1, 2, 3, 4, 5 or 6 and
n is 1, 2, 3, 4, 5, 6, 7, 8, 9, 10, 11, 12 or 13, and their salts.

Thiadiazinones are known from DE 3,719,031 Al and its U.S. counterpart, U.S. Pat. No. 4,916,128.

The invention was based on the object of finding novel compounds with useful properties, in particular those which can be used for the production of medicaments.

It has been found that the compounds of the formula I have useful pharmacological properties, coupled with good tolerability. In particular, they exhibit an action on the force of the heart (positively inotropic activity); the substances furthermore have a vasodilating action and therefore promote circulation. The vasodilating action and the cardiac action can be determined, for example, on anaesthetised or conscious dogs, cats, monkeys or mini-pigs, and the positively inotropic action can also be determined on isolated heart preparations (for example atrium, papillary muscle or perfused whole heart) from rats, guinea-pigs, cats or dogs, for example in accordance with methods such as are described in Arzneimittelforschung, Volume 31 (1) No. 1a (1981), pages 141 to 170, or by Schliep et al. in the 9th International Congress of Pharmacol., London, Abstracts of papers 9P.

In addition, the compounds can be employed for the treatment of asthmatic diseases. The antiasthmatic action can be determined, for example, in accordance with the method of T. Olsson, Acta Allergologica 26, 438–447 (1971).

The compounds also have a cerebroprotective effect, can be employed for the treatment of memory disorders and have antidepressive and anti-inflammatory properties.

The compounds can therefore be used as pharmaceutical active substances in human and veterinary medicine. They can also be used as intermediates for the preparation of further pharmaceutical active substances.

The invention accordingly relates to the compounds of the formula I and to a process for their preparation, characterized in that a compound of the formula II

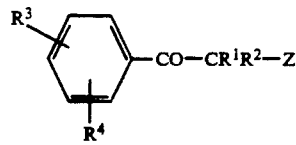

in which $R^1$, $R^2$, $R^3$ and $R^4$ have the meanings indicated and Z is Br, Cl, I or a reactive esterified OH group, is reacted with a compound of the formula III

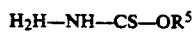

$$H_2H-NH-CS-OR^5 \quad \text{III}$$

in which
$R^5$ is A, ammonium, Na or K
and A has the meaning indicated,
and/or in that a compound which corresponds to the formula I, but instead of $R^3$ and/or $R^4$ contains one or two free OH groups, is optionally reacted with a compound of the formula $R^3-Z$ or $R^4-Z$, in which $R^3$, $R^4$ and Z have the meanings indicated, and/or a base of the formula I is converted into one of its salts by treatment with an acid.

Hereinbefore and hereinafter, the radicals $R^1$ to $R^4$, $R^5$, A, X and Z and the parameters m and n have the meanings indicated in the formulae I, II and III, if not expressly stated otherwise.

In the formulae, alkyl is preferably unbranched, preferably has 1, 2, 3 or 4 C atoms and is preferably methyl, also preferably ethyl or propyl, and furthermore preferably isopropyl, butyl, isobutyl, sec-butyl or tertbutyl, but also n-pentyl or isopentyl.

Alkoxy is preferably unbranched, preferably has 1, 2 or 3 C atoms and is preferably methoxy, also preferably ethoxy or propoxy, and furthermore, for example, isopropoxy, butoxy, isobutoxy, sec-butoxy, tert-butoxy, pentoxy or isopentoxy.

In detail, the radicals $R^1$, $R^2$, $R^3$ and $R^4$ have the following preferred meanings: $R^1$ is H; $R^2$ is methyl or ethyl; $R^3$ is methoxy and $R^4$ is difluoromethoxy. If the radicals $R^3$ and/or $R^4$ are other than H, they are preferably in the 3- or 4-position of the phenyl ring. The radical X is preferably F. The parameters m and n are ably in the 3- or 4-position of the phenyl ring. The radical X is preferably F. The parameters m and n are preferably selected so that $2m+1 \geq n$, with all valences on carbon satisfied.

The invention relates in particular to those compounds of the formula I in which at least one of the said radicals has one of the abovementioned preferred meansings. Some preferred groups of compounds can be expressed by the following part-formulae Ia to Id, which correspond to the formula I and in which the radicals not designated in greater detail have the meaning indicated in the formula I, but in which in Ia $R^3$ is in the 4-position and $R^4$ in the 3-position of the phenyl ring,
$R^1$ is H,
$R^2$ is H or alkyl,
$R^3$ is $OCHF_2$ and
$R^4$ is OA;
in Ib $R^3$ is in the 4-position and $R^4$ in the 3-position of the phenyl ring,
$R^1$ is H,
$R^2$ is methyl or ethyl,
$R^3$ is $OCHF_2$ and
$R^4$ is OA;

in Ic $R^3$ is in the 4-position and $R^4$ in the 3-position of the phenyl ring,
$R^1$ is H,
$R^2$ is methyl or ethyl,
$R^3$ is $OCHF_2$, $OCF_3$, $OC_2H_{5-n}P_n$, where n=1, 2, 3, 4 or 5 and
$R^4$ is OA;
in Id $R^3$ is in the 4-position and $R^4$ in the 3-position of the phenyl ring,
$R^1$ is H,
$R^2$ is methyl or ethyl,
$R^3$ is $OCHF_2$, $OCF_3$, $OC_2H_{5-n}F_n$, $OC_3H_{7-n}F_n$, where n=1, 2, 3, 4, or 5, $OC_3H_{7-n}F_n$ or $OC_4H_{9-n}F_n$ where n=6 or 7, or $OC_4H_{9-n}F_n$ where n=8 or 9 and
$R^4$ is OMe or OEt.

The compounds of the formula I are otherwise prepared by methods known per se, as are described in the literature (for example in the standard works such as Houben-Weyl, Methoden der Organischen Chemie (Methods of Organic Chemistry), Georg-Thieme-Verlag, Stuttgart), to be precise under reaction conditions which are known and suitable for the said reactions. In this connection, use can also be made of variants which are known per se but not mentioned here in greater detail.

In the compounds of the formula II, $R^1$, $R^2$, $R^3$ and $R^4$ have the meanings indicated, while Z is preferably Cl or Br. If X is a reactive esterified OH group, this is preferably alkysulphonyloxy having 1–6 C atoms, for example methanesulphonyloxy or arylsulphonyloxy having 6–10 C atoms, for example benzene-, p-toluene- or 1- or 2-naphthalenesulphonyloxy.

In the compounds of the formula III, $R^5$ is preferably methyl or ethyl, but also Na, K or ammonium.

If desired, the starting substance can also be formed in situ, such that they are not isolated from the reaction mixture, but immediately reacted again to give the compounds of the formula I. On the other hand, it is possible to carry out the reaction stepwise, it being possible to isolate further intermediates.

The starting substances of the formulae II and III are known in some cases. If they are not known, they can be prepared by methods known per se. The ketones of the formula II are accessible, for example, by FriedelCrafts synthesis from the corresponding phenyl derivatives using compounds of the formula $Y-CO-CR^1R^2-Z$, where Y is Cl or Br.

In detail, the reaction of the ketones of the formula II with the compounds of the formula III is carried out in the presence or absence of an inert solvent at temperatures between about $-20°$ and about $+150°$, preferably between 20° and 100°. Suitable solvents are, for example, hydrocarbons such as benzene, toluene, xylenes or mesitylene; halogenated hydrocarbons such as dichloromethane, trichloroethylene or chlorobenzene; alcohols such as methanol, ethanol or isopropanol; glycols and glycol ethers such as ethylene glycol, diethylene glycol, 2-methoxyethanol; nitriles such as acetonitrile; ethers such as tetrahydrofuran or dioxane; amides such as dimethylformamide (DMF); sulphoxides such as dimethyl sulphoxide. Mixtures of these solvents are also suitable.

It is also possible to react a compound which corresponds to the formula I, but instead of $R^3$ and/or $R^4$ contains one or two free OH groups, with a compound of the formula $R^3-Z$ or $R^4-Z$ in which $R^3$, $R^4$ and Z have the meanings indicated. The OH groups are etherified by methods known per se, such as are described in standard works of the chemical literature (for example in Houben-Weyl, Methoden der Organischen Chemie (Methods of Organic Chemistry), Georg Thieme Verlag, Stuttgart or in Organic Reactions, John Wiley & Sons Inc., New York), to be precise under reaction conditions as are known and suitable for the said reactions. In this connection, use can also be made of variants which are known per se but not mentioned here in greater detail.

Compounds of the formula I can contain one or more centres of asymmetry. In this case, they are usually present in racemic form. Racemates obtained can be resolved mechanically or chemically into their optical antipodes by methods known per se. Preferably, diastereomers are formed from the racemic mixture by reaction with an optically active resolving agent.

Of course, it is also possible to obtain optically active compounds of the formula I by the methods described above by using starting substances which are already optically active.

The invention also relates to the use of the compounds of the formula I and of their physiologically acceptable salts for the production of pharmaceutical preparations, in particular by non-chemical routes. In this connection, they can be brought into a suitable dosage form together with at least one solid, liquid and/or semi-liquid excipient or auxiliary and optionally in combination with one or more further active substances.

The invention also relates to compositions, in particular pharmaceutical preparations, containing at least one compound of the formula I and/or one of its physiologically acceptable salts.

These preparations can be used as medicaments in human or veterinary medicine. Possible excipients are organic or inorganic substances which are suitable for enteral (for example oral), parenteral or topical administration and do not react with the novel compounds, for example water, vegetable oils, benzyl alcohols, polyethylene glycols, glycerol triacetate, gelatine, carbohydrates such as lactose or starch, magnesium stearate, talc and petroleum jelly. Tablets, coated tablets, capsules, syrups, juices or drops are used for oral administration, suppositories for rectal administration, solutions, preferably oily or aqueous solutions, and also suspensions, emulsions or implants are used for parenteral administration, and ointments, creams or powders are used for topical application. The novel compounds can also be lyophilised and the lyophilisates obtained used, for example, for the production of injection preparations. The preparations indicated can be sterilised and/or contain auxiliaries such as lubricants, preservatives, stabilisers and/or wetting agents, emulsifiers, salts for affecting the osmotic pressure, buffer substances, colourants, flavourings and/or aromatic substances. They can also contain, if desired, one or more other active substances, for example one or more vitamins.

The compounds of the formula I can be used in the control of diseases, in particular of cardiac insufficiency, and in the therapeutic treatment of the human or animal body.

In this connection, the substances according to the invention are as a rule administered in analogy to known positively inotropically active substances such as amrinone, preferably in dosages between about 1 and 100 mg, in particular between 2 and 20 mg per dosage unit. The daily dosage is preferably between about 0.02 and 2 mg/kg of body weight. The particular dose for each specific patient depends, however, on all sorts of factors, for example on the activity of the particular compound employed, on the age, body weight, general state of health, sex, on the diet, on the administration time and route, on the excretion rate, pharmaceutical combination and severity of the particular disease to which the therapy applies. Oral administration is preferred. In comparison to the digitalis glycosides used to date for the therapy of cardiac insufficiency, the compounds of the formula I are distinguished by improved therapeutic breadth and release of peripheral strain.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 41 34 893.1, are hereby incorporated by reference.

In the following examples "customary working up" means:

If necessary, water or dilute sodium hydroxide solution is added, the mixture is extracted with an organic solvent such as ethyl acetate, chloroform or dichloromethane, the extract is separated off, the organic phase is dried over sodium sulphate, filtered and evaporated, and the residue is purified by chromatography and/or crystallisation.

EXAMPLE 1

A solution of 7.0 g of 1-(3-methoxy-4difluoromethoxyphenyl)-2-bromobutan-1-one [obtainable by etherification of 1-(4-hydroxy-3-methoxyphenyl)butan-1-one with chlorodifluoromethane and subsequent bromination] in 50 ml of acetonitrile is boiled for 2 hours with 2.6 g of methyl hydrazinothioformate.

The solvent is then removed in vacuo and the residue is worked up in the customary manner. 5-(3-Methoxy-4-difluoromethoxyphenyl)-6-ethyl-3,6-dihydro-1,3,4-thiadiazin-2-one, m.p. 97°, is obtained.

The following are obtained analogously by reaction of methyl hydrazinothioformate with
1-(3-methoxy-4-trifluoromethoxyphenyl)-2-bromobutan-1-one:
  5-(3-methoxy-4-trifluoromethoxyphenyl)-6-ethyl-3,6-dihydro-1,3,4-thiadiazin-2-one;
1-(3-methoxy-4-trifluoromethoxyphenyl)-2-bromopropan-1-one:
  5-(3-methoxy-4-trifluoromethoxyphenyl)-6-methyl-3,6-dihydro-1,3,4-thiadiazin-2-one;
1-(3-methoxy-4-difluoromethoxyphenyl)-2-bromopropan-1-one:
  5-(3-methoxy-4-difluoromethoxyphenyl)-6-methyl-3,6-dihydro-1,3,4-thiadiazin-2-one;
1-[3-methoxy-4-(1,1,2,2-tetrafluoroethoxy)phenyl]-2-bromobutan-1-one:
  5-[3-methoxy-4-(1,1,2,2-tetrafluoroethoxy)phenyl]-6-ethyl-3,6-dihydro-1,3,4-thiadiazin-2-one;
1-(3-methoxy-4-chloromethoxyphenyl)-2-bromobutan-1-one:
  5-(3-methoxy-4-chloromethoxyphenyl)-6-ethyl-3,6-dihydro-1,3,4-thiadiazin-2-one;
1-(3-methoxy-4-chloromethoxyphenyl)-2-bromopropan-1-one:
  5-(3-methoxy-4-chloromethoxyphenyl)-6-methyl-3,6-dihydro-1,3,4-thiadiazin-2-one;
1-(3-methoxy-4-pentachloroethoxyphenyl)-2-bromobutan-1-one:
  5-(3-methoxy-4-pentachlorethhoxyphenyl)-6-ethyl-3,6-dihydro-1,3,4-thiadiazin-2-one;
1-(3-methoxy-4-trifluoromethoxyphenyl)-2-bromopentan-1-one:
  5-(3-methoxy-4-trifluoromethoxyphenyl)-6-propyl-3,6-dihydro-1,3,4-thiadiazin-2-one;
1-(3-methoxy-4-difluoromethoxyphenyl)-2-bromopentan-1-one:
  5-(3-methoxy-4-difluoromethoxyphenyl)-6-propyl-3,6-dihydro-1,3,4-thiadiazin-2-one;
1-[3-methoxy-4-(1,1,2-trifluoroethoxy)phenyl[-2-bromobutan-1-one:
  5-[3-methoxy-4-(1,1,2-trifluoroethoxy)phenyl]-6-ethyl-3,6-dihydro-1,3,4-thiadiazin-2-one;
1-[3-methoxy-4-(1,1,2-trifluoroethoxy)phenyl]-2-bromopropan-1-one;
  5-[3-methoxy-4-(1,1,2-trifluoroethoxy)phenyl]-6-methyl-3,6-dihydro-1,3,4-thiadiazin-2-one.

EXAMPLE 2

Analogously to Example 1, the following is obtained by reaction of methyl hydrazinothioformate with 1-(4-difluoromethoxy-3-methoxyphenyl)-2-bromoethan-1-one: 5-(3-methoxy-4-difluoromethoxyphenyl)-3,6-dihydro-1,3,4-thiadiazin-2-one, m.p. 120°.

The following are obtained analogously by reaction of methyl hydrazinothioformate with
1-(3-methoxy-4-trifluoromethoxyphenyl)-2-bromoethan-1-one:
  5-(3-methoxy-4-trifluoromethoxyphenyl)-3,6-dihydro-1,3,4-thiadiazin-2-one;
1-(4-trifluoromethoxyphenyl)-2-bromoethan-1-one:
  5-(4-trifluoromethoxyphenyl)-3,6-dihydro-1,3,4-thiadiazin-2-one;
1-(3-methoxy-4-difluoromethoxyphenyl)-2-bromoethan-1-one:
  5-(3-methoxy-4-difluoromethoxyphenyl)-3,6-dihydro-1,3,4-thiadiazin-2-one;
1-[3-methoxy-4-(1,1,2,2-tetrafluoroethoxy)phenyl]-2-bromoethan-1-one:
  5-[3-methoxy-4-(1,1,2,2-tetrafluoroethoxy)phenyl]-3,6-dihydro-1,3,4-thiadiazin-2-one;
1-(3-methoxy-4-chloromethoxyphenyl)-2-bromoethan-1-one;
  5-(3-methoxy-4-chloromethoxyphenyl)-3,6-dihydro-1,3,4-thiadiazin-2-one;
1-(3-methoxy-4-trichloromethoxyphenyl)-2-bromoethan-1-one;
  5-(3-methoxy-4-trichloromethoxyphenyl)-3,6-dihydro-1,3,4-thiadiazin-2-one;
1-(3-methoxy-4-pentachloroethoxyphenyl)-2-bromoethan-1-one;
  5-(3-methoxy-4-pentachloroethoxyphenyl)-3,6-dihydro-1,3,4-thiadiazin-2-one;
1-(4-difluoromethoxyphenyl)-2-bromoethan-1-one;
  5-(4-difluoromethoxyphenyl)-3,6-dihydro-1,3,4-thiadiazin-2-one.

EXAMPLE 3

A solution of 5.4 g of 5-(3-methoxy-4-hydroxyphenyl)-6-ethyl-3,6-dihydro-1,3,4-thiadiazin-2-one [obtainable by reaction of 1-(4-hydroxy-3-methoxyphenyl)-2-bromobutan-1-one with methyl hydrazinothioformate] in THF is boiled for two hours after addition of one equivalent of 3-iodo-1,1,2,2,3-pentafluoropropane. The solvent is then removed in vacuo and the mixture is worked up in the customary manner. 5-[3-Methoxy-4-(1,1,2,2,3-pentafluoropropoxyphenyl)]-6-ethyl-3,6-dihydro-1,3,4-thiadiazin-2-one is obtained.

The following are obtained analogously by etherification of the corresponding mono- or dihydroxyphenyl-1,3,4-thiadiazinone derivatives with polyfluoroalkyl halides:

5-(3-methoxy-4-trifluoromethoxyphenyl)-3,6-dihydro-1,3,4-thiadiazin-2-one;

5-(4-trifluoromethoxyphenyl)-3,6-dihydro-1,3,4-thiadiazin-2-one;

5-[bis-3,4-difluoromethoxy)phenyl]-3,6-dihydro-1,3,4-thiadiazin-2-one;

5-[3-methoxy-4-(1,1,2-trifluoroethoxy)phenyl]-3,6-dihydro-1,3,4-thiadiazin-2-one;

5-[bis-3,4-(dichloromethoxy)phenyl]-3,6-dihydro-1,3,4-thiadiazin-2-one.

EXAMPLE 4

Analogously to Example 1, 5-[bis-3,4-(difluoromethoxy)phenyl]-3,6-dihydro-1,3,4-thiadiazin-2-one is obtained by reaction of methyl hydrazinothioformate with 1-[bis-3,4-(difluoromethoxy)phenyl]-2-bromoethan-1-one.

The following are obtained analogously by reaction of methyl hydrazinothioformate with 1-[bis-3,4-(trifluoromethoxy)phenyl]-2-bromoethan-1-one:
  5-[di-(3,4-trifluoromethoxy)phenyl]-3,6-dihydro-1,3,4-thiadiazin-2-one;

1-[bis-3,4-(difluoroethoxy)phenyl]-2-bromoethan-1-one:
  5-[bis-3,4-(1,2-difluoroethoxy)phenyl]-3,6-dihydro-1,3,4-thiadiazin-2-one;

1-[3-ethoxy-4-(1,1,2,2-tetrafluoroethoxy)phenyl]-2-bromoethan-1-one:
  5-[3-ethoxy-4-(1,1,2,2-tetrafluoroethoxy)phenyl]-3,6-dihydro-1,3,4-thiadiazin-2-one;

1-[3-methoxy-4-(1,2,2-trichloroethoxy)phenyl]-2-bromoethan-1-one:
  5-[3-ethoxy-4-(1,2,2-trichloroethoxy)phenyl]-3,6-dihydro-1,3,4-thiadiazin-2one.

EXAMPLE 5

The following are obtained analogously to Example 1 by reaction of methyl hydrazinothioformate with:

1-(2-methoxy-3-difluoromethoxyphenyl)-2-bromoethan-1-one:
  5-(2-methoxy-3-difluoromethoxyphenyl)-3,6-dihydro-1,3,4-thiadiazin-2-one;

1-(2-ethoxy-4-trifluoromethoxyphenyl)-2-bromoethan-1-one:
  5-(2-ethoxy-4-trifluoromethoxyphenyl)-3,6-dihydro-1,3,4-thiadiazin-2-one;

1-(2-trifluoromethoxyphenyl)-2-bromoethan-1-one:
  5-(2-trifluormethoxyphenyl)-3,6-dihydro-1,3,4-thiadiazin-2-one;

1-(2-ethoxy-3-difluoromethoxyphenyl)-2-bromoethan-1-one:
  5-(2-ethoxy-3-difluoromethoxyphenyl)-3,6-dihydro-1,3,4-thiadiazin-2-one;

1-[2-(1,1,2,2-tetrafluoroethoxy)phenyl]-2-bromoethan-1-one:
  5-[2-(1,1,2,2-tetrafluoroethoxy)phenyl]-3,6-dihydro-1,3,4-thiadiazin-2-one;

1-(3-methoxy-5-chloromethoxyphenyl)-2-bromoethan-1-one:
  5-(3-methoxy-5-chloromethoxyphenyl)-3,6-dihydro-1,3,4-thiadiazin-2-one;

1-(3-methoxy-5-trichloromethoxyphenyl)-2-bromoethan-1-one:
  5-(3-methoxy-5-trichloromethoxyphenyl)-3,6-dihydro-1,3,4-thiadiazin-2-one;

1-(2-methoxy-4-pentachloroethoxyphenyl)-2-bromoethan-1-one:
  5-(2-methoxy-4-pentachloroethoxyphenyl)-3,6-dihydro-1,3,4-thiadiazin-2-one;

1-(2-difluoromethoxyphenyl)-2-bromoethan-1-one:
  5-(2-difluoromethoxyphenyl)-3,6-dihydro-1,3,4-thiadiazin-2-one.

EXAMPLE 6

Analogously to Example 1, 5-[4-(2.2.2-trifluoroethoxy)phenyl]-6-ethyl-3.6-dihydro-1.3.4-thiadiazin-2-one, m.p. 102°, is obtained by reaction of methyl hydrazinothioformate with 1-[4-(2.2.2-trifluoroethoxy)phenyl]-2-bromobutan-1-one.

The following are obtained analogously by reaction of methyl hydrazinothioformate with:

1-[3-methoxy-4-(2.2.2-trifluoroethoxy)phenyl]-2-bromo-1-one:
  5-[3-methoxy-4-(2.2.2-trifluoroethoxy)phenyl]-6-ethyl-3.6-dihydro-1.3.4-thiadiazin-2-one, m.p. 123°–125°;

1-[3-methoxy-4-(2.2.2-trifluoroethoxy)phenyl]-2-bromoethan-1-one:
  5-[3-methoxy-4-(2.2.2-trifluoroethoxy)phenyl]-3.6-dihydro-1.3.4-thiadiazin-2-one, m.p. 120°;

1-[3-(2.2.2-trifluoroethoxy)4-methoxy-phenyl]-2-bromobutan-1-one:
  5-[3-(2.2.2-trifluoroethoxy)-4-methoxy-phenyl]-6-ethyl-3.6-dihydro-1.3.4-thiadiazin-2-one, m.p. 120°–121°;

1-[3-difluoromethoxy-4-methoxy-phenyl)-2-bromobutan-1-one:
  5-[3-difluoromethoxy-4-methoxy-phenyl)-6-ethyl-3.6-dihydro-1.3.4-thiadiazin-2-one, m.p. 105°.

EXAMPLE 7

Chromatographical separation of racemic 5-(3-methoxy-4-difluoromethoxy-phenyl)-6-ethyl-3.6-dihydro-1.3.4-thiadiazin-2-one [m.p. 97°%; obtainable according to example 1] using a chiral stationary phase (ChiraSpher ®)) yields:

(+)-5-(3-methoxy-4-difluoromethoxy-phenyl)-6-ethyl-3.6-dihydro-1.3.4-thiadiazin-2-one and (−)-5-(3-methoxy-4-difluoromethoxy-phenyl)-6-ethyl-3.6-dihydro-1.3.4-thiadiazin-2-one.

Analogously one obtains by chromatographical separation of racemic 5-[3-(2.2.2-trifluoroethoxy)-4-methoxy-phenyl]-6-ethyl-3.6-dihydro-1.3.4-thiadiazin-2-one [m.p. 120°–121°; obtainable according to example 6]:

(+)-5-[3-(2.2.2-trifluoroethoxy)-4-methoxy-phenyl]-6-ethyl-3.6-dihydro-1.3.4-thiadiazin-2-one and (−)-5-[3-(2.2.2-trifluoroethoxy)-4-methoxy-phenyl]-6-ethyl-3.6-dihydro-1.3.4-thiadiazin-2-one.

The examples hereinafter relate to pharmaceutical preparations which contain compounds of the formula I or their acid addition salts:

EXAMPLE A

Tablets

A mixture of 1 kg of 5-(3-methoxy-4-difluoromethoxyphenyl)-6-ethyl-3,6-dihydro-1,3,4-thiadiazin-2-one, 10 kg of lactose, 6 kg of microcrystalline cellulose, 6 kg of potato starch, 1 kg of polyvinylpyrrolidone, 0.8 kg of talc and 0.1 kg of magnesium stearate is pressed to give tablets in a customary manner such that each tablet contains 10 mg of active substance.

EXAMPLE B

Coated tablets

Tablets are pressed analogously to Example A and are subsequently coated in a customary manner with a coating of sucrose, potato starch, talc, tragacanth and colourant.

EXAMPLE C

Capsules 1 kg of 5-(3-methoxy-4-difluoromethoxyphenyl)-3,6-dihydro-1,3,4-thiadiazin-2-one is filled into hard gelatin capsules in a customary manner such that each capsule contains 5 mg of active substance.

EXAMPLE D

Ampoules

A solution of 1 kg of 5-(3-methoxy-4-difluoromethoxyphenyl)-3,6-dihydro-1,3,4-thiadiazin-2-one in 30 l of 1,2-propanediol is sterile-filtered, filled into ampoules and lyophilised under sterile conditions, and the ampoules are sealed under sterile conditions. Each ampoule contains 2 mg of active substance.

Tablets, coated tablets, capsules and ampoules which contain one or more of the other active substances of the formula I and/or their physiologically acceptable acid addition salts can be obtained analogously.

The preceding examples can be repeated with similar success by substituting the generically or specifically described reactants and/or operating conditions of this invention.

From the foregoing description, one skilled in the art can easily ascertain the essential characteristics of this invention, and without departing from the spirit and scope thereof, can make various changes and modifications of the invention to adapt it to various usages and conditions.

We claim:

1. A thiadiazinone compound of formula I

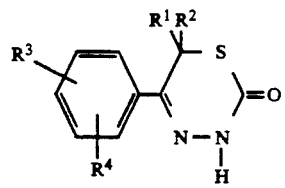

in which
$R^1$ and $R^2$ are each independently of one another H or A,
$R^3$ is H, OA, or $O-C_mH_{2m+1-n}X_n$,
$R^4$ is $-O-C_mH_{2m+1-n}X_n$,
X is F or Cl,
A is $C_{1-6}$ alkyl,
m is 1, 2, 3, 4, 5 or 6 and
n is 1, 2, 3, 4, 5, 6, 7, 8, 9, 10, 11, 12 or 13,
or a salt thereof.

2. A compound according to claim 1, wherein m is 1-3 and n is 1-7.

3. A compound according to claim 1, wherein $R^1$ is H, $R^2$ is methyl or ethyl, $R^3$ is methoxy and $R^4$ is difluoromethoxy.

4. A compound according to claim 1, wherein $R^3$ is in the 4-position and $R^4$ in the 3-position of the phenyl ring,
$R^1$ is H,
$R^2$ is H or alkyl,
$R^3$ is $OCHF_2$ and
$R^4$ is OA.

5. A compound according to claim 1, wherein $R^3$ is in the 4-position and $R^4$ in the 3-position of the phenyl ring,
$R^1$ is H,
$R^2$ is methyl or ethyl,
$R^3$ is $OCHF_2$ and
$R^4$ is OA.

6. A compound according to claim 1, wherein $R^3$ is in the 4-position and $R^4$ in the 3-position of the phenyl ring,
$R^1$ is H,
$R^2$ is methyl or ethyl,
$R^3$ is $OCHF_2$, $OCF_3$, $OC_2H_{5-n}F_n$, where n=1, 2, 3, 4, or 5 and
$R^4$ is OA.

7. A compound according to claim 1, wherein $R^3$ is in the 4-position and $R^4$ in the 3-position of the phenyl ring,
$R^1$ is H,
$R^2$ is methyl or ethyl,
$R^3$ is $OCHF_2$, $OCF_3$, $OC_2H_{5-n}F_n$, $OC_3H_{7-n}F_n$, where n=1, 2, 3, 4, or 5, $OC_3H_{7-n}F_n$ or $OC_4H_{9-n}F_n$ where n=6 or 7, or $OC_4H_{9-n}F_n$ where n=8 or 9 and
$R^4$ is OMe or OEt.

8. a) 5-(3-Methoxy-4-difluoromethoxyphenyl)-6-ethyl-3,6-dihydro-1,3,4-thiadiazin-2-one; or b) 5-(3-methoxy-4-difluoromethoxyphenyl)-3,6-dihydro-1,3,4-thiadiazin-2-one, each a compound of claim 1.

9. A pharmaceutical composition comprising a compound of claim 1 and a physiologically acceptable carrier.

10. A method of treating cardiac insufficiency, comprising administering an effective amount of a compound of claim 1.

11. A method of treating asthma, comprising administering an effective amount of a compound of claim 1.

* * * * *